United States Patent

Guendel

[11] Patent Number: 5,315,628
[45] Date of Patent: May 24, 1994

[54] COMPUTER TOMOGRAPH HAVING MEANS FOR DISPLAYING SHADOWGRAPHS

[75] Inventor: Lutz Guendel, Erlangen, Fed. Rep. of Germany

[73] Assignee: Siemens Aktiengesellschaft, Munich, Fed. Rep. of Germany

[21] Appl. No.: 73,515

[22] Filed: Jun. 9, 1993

[30] Foreign Application Priority Data

Jun. 24, 1992 [DE] Fed. Rep. of Germany ....... 4220709
Jul. 16, 1992 [DE] Fed. Rep. of Germany ....... 4223430

[51] Int. Cl.$^5$ ............................................... A61B 6/03
[52] U.S. Cl. ......................................... 378/20; 378/4; 378/146
[58] Field of Search ............... 378/4, 20, 8, 14, 62, 378/205, 207, 146

[56] References Cited

U.S. PATENT DOCUMENTS

| | | |
|---|---|---|
| 4,174,481 | 11/1979 | Liebetruth . |
| 4,216,526 | 8/1980 | Karwoski . |
| 4,352,986 | 10/1982 | Pfeiler . |
| 4,477,922 | 10/1984 | Liebetruth ........................ 378/4 X |
| 4,570,263 | 2/1986 | Liebetruth ........................ 378/4 X |
| 4,624,007 | 11/1986 | Muranushi ............................ 378/4 |
| 5,212,717 | 5/1993 | Hada ..................................... 378/4 |

FOREIGN PATENT DOCUMENTS

2939975 4/1981 Fed. Rep. of Germany .
4103588 5/1992 Fed. Rep. of Germany .

Primary Examiner—David P. Porta

[57] ABSTRACT

A medical imaging apparatus includes a measurement unit with an x-ray source and a radiation detector rotatable around an examination subject to conduct a scan of the examination subject and thereby to obtain a data set, which is supplied to a computer. Within the computer, a shadowgraph of the examination subject is calculated in real time as the examination subject is displaced during the scan relative to the measurement unit. The data used to construct the shadowgraph are obtained at a selected projection angle, which is reached a number of times by the measurement unit during the scan. The shadowgraph is displayed in real time as well, to an extent correlated with the amount of relative displacement between the examination subject and the measurement unit. The shadowgraph can be calculated using a convolution equation, wherein the data are twice convolved, once in the longitudinal direction, i.e., the direction of displacement between the examination subject and the measurement unit, and once in a direction corresponding to the direction along which the radiation detector extends. A standard computer tomogram can also be calculated from the same data set from which the data for calculating the shadowgraph are selected.

4 Claims, 1 Drawing Sheet

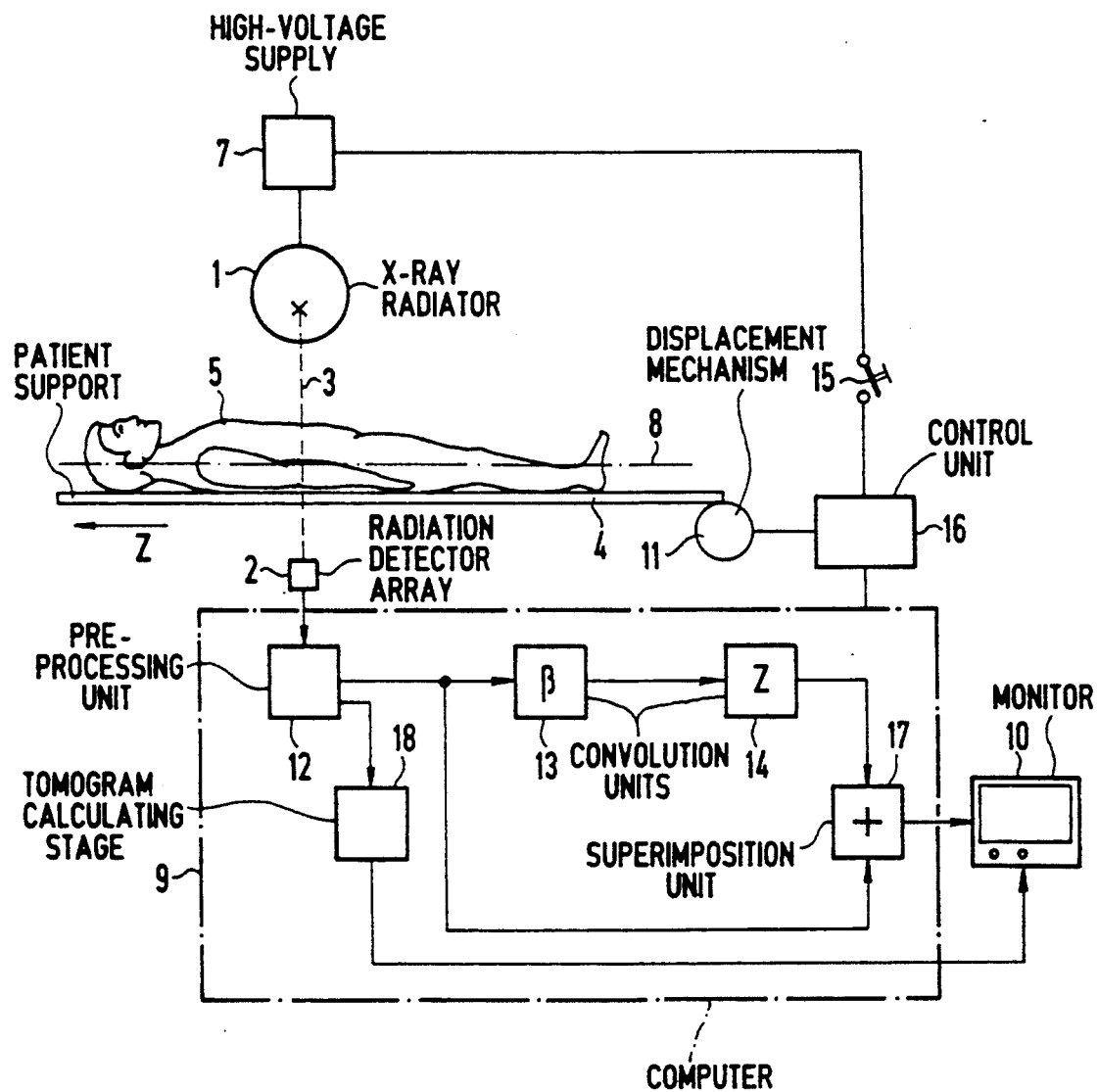

COMPUTER TOMOGRAPH HAVING MEANS FOR DISPLAYING SHADOWGRAPHS

BACKGROUND OF THE INVENTION

1. Field of the Invention

The present invention is directed to a computer tomography apparatus of the type wherein the detector signals can also be processed to calculate a shadowgraph of the examination subject.

2. Description of the Prior Art

In a so-called third generation computer tomography apparatus, it is known to rotate the measurement unit, for portraying a specific slice of the examination subject, by 360° around the system axis and to calculate the computer tomogram from the output signals of the detector array. For defining the layer that is computer-tomographically displayed, the measuring unit is interlocked in a predetermined angular position to prevent rotation and a relative displacement between the measuring unit and the patient support ensues proceeding from a starting position. The length for this relative displacement is preset. Subsequently, radiation is triggered and the output signals of the detector array are acquired by the computer during the scanning. Only when the pre-set relative displacement has been completed, which corresponds to the desired length of the shadowgraph, is the shadowgraph calculated from the intermediately stored and partially processed output signals of the detector array. The calculation of the shadowgraph thus only ensues after the patient support has reached the pre-set final position.

The pre-setting of the length of the shadowgraph constitute an additional operating event. Since the portrayal of the shadow-graph ensues only after the measurement, it is possible that either too short or too long a measurement ensues. In the former instance, the exposure of the shadowgraph must be repeated; in both instances, the patient is exposed to unnecessary radiation.

It is also known to fashion a computer tomograph of the third or fourth generation such that a shadowgraph can be simultaneously produced with the tomographic exposure as disclosed in German Patent 41 03 588.

SUMMARY OF THE INVENTION

It is an object of the present invention to specify a teaching for producing substantially artifact-free shadowgraphic images from data obtained from the radiation detector in a computer tomography apparatus with the shadowgraph being displayable to an extent corresponding to the progress of the relative displacement of the subject and the measurement unit.

The above object is achieved in accordance with the principles of the present invention in a medical imaging apparatus having a measurement unit with an x-ray source and a radiation detector which is rotatable around an examination subject to conduct a scan of the subject and thereby to obtain a data set, which is supplied to a computer. A shadowgraph of the examination subject is calculated in real time in the computer as the examination subject is displaced during the scan relative to the measurement unit. The data used to construct the shadowgraph are obtained at a selected projection angle, which is reached a number of times by the measurement unit during the scan. The shadowgraph is displayed in real time as well, to an extent correlated with the amount of relative displacement between the examination subject and the measurement unit.

The shadowgraph can be calculated using a convolution equation, wherein the data are twice convolved, once in the longitudinal direction, i.e., the direction of displacement between the examination subject and the measurement unit, and once in a direction corresponding to the direction along which the radiation detector extends.

In the computer tomography apparatus of the invention, the shadowgraph is already displayed on a monitor during the relative displacement between the patient support and the measuring unit, the extent of the displayed shadowgraph corresponding to the progress of this relative displacement. When the physician recognizes the desired measurement field in the shadowgraph for the production of a computer tomogram he or she can end the measurement for generating the shadowgraph.

DESCRIPTION OF THE DRAWINGS

The single FIGURE is a schematic illustration of a medical imaging apparatus constructed in accordance with the principles of the present invention.

DESCRIPTION OF THE PREFERRED EMBODIMENTS

The drawing shows a measuring unit composed of an x-radiator 1 and a detector array 2 that extends perpendicular to the plane of the drawing and is composed of a row of detector elements. A fan-shaped x-ray beam 3 is generated by the x-ray radiator 1 in a fan plane proceeding perpendicular to the plane of the drawing and which penetrates a patient 5 lying on a patient support 4 and is incident on the detector array 2. The x-ray radiator 1 is fed by an high-voltage generator 7.

For preparing computer tomograms, a prescribed slice of the patient 5 is scanned by rotating the measuring unit, consisting of the x-ray radiator 1 and the detector array 3 and thus the x-ray beam 3, through 360° around a system axis 8. A computer 9 calculates a computer tomogram from the output signals of the detector array 2 after pre-processing in a pre-processing unit 12, and effects the reproduction of this computer tomogram on a monitor 10.

For defining the position of the slice, shadowgraphs can also be produced with the illustrated computer tomograph. This can be accomplished for example by interlocking the measuring unit in a predetermined angular position to prevent rotation and a relative displacement between the measuring unit and the patient support 4 ensues by moving the patient support 4 in the longitudinal direction, i.e., in the Z-direction, with a displacement mechanism 11, while the x-radiator 1 is activated and the output signals of the detector array 2 are required by the computer 9. Alternatively, a single set of tomographic data can be obtained using, for example, a helical scan, and the data for use in calculating the shadowgraph can be selected from the tomographic data for a given single projection angle which is repeatedly reached by the measurement unit during the helical scan.

In the computer 9, the shadowgraph data are supplied to a pre-processing unit 12 is followed by a convolution unit 13 for convolution in the $\beta$ direction and a convolution unit 14 for convolution in the Z-direction. The $\alpha$ direction is thereby the longitudinal direction of the detector array 2. A superimposition of the convoluted and the non-convoluted information in a superimposition unit 17 and a display of the shadowgraph on the monitor 10 subsequently ensue. The amount (extent) of the displayed shadowgraph corresponds to the extent of the patient 5 which has passed through the plane of the fan beam 3.

The convolution in Z-direction is implemented on the basis of direct convolution, according to the equation:

$$b_l(k) = \sum_{\chi=-n/2}^{n/2} U_l(k - \chi) \times h(\chi),$$

wherein
l is the index in the $\beta$-direction,
k is the index in the Z-direction,
$\chi$ is the numerical index for the convolution,
$u_l$ (k) is the convolved readings in the $\beta$-direction (measurement of the attenuation values of a slice),
$b_l(k)$ is the readings additionally convolved in the Z-direction,
h is the convolution core,
n is the degree of the convolution core, and
$\beta$ is the direction of the extent of the detector array 2 (into and out of the plane of the drawing, in that exemplary embodiment).

After each convolution step, the data $b_1(O)$ through $b_1(k)$ are superimposed weighted line-by-line and are displayed at the monitor 10. The last n/2 lines in fact represent only an intermediate result; however, they coincide as much as possible with the desired result. A high-contrast direct image can thus be displayed, and the disadvantages initially set forth can be avoided.

A realization with "fast convolution", i.e. calculation via the discrete Fourier transformation and its inverse, is thus not precluded.

The exposure of a shadowgraph ensues upon the pressing of a key 15 by the physician. As a result, the radiation is activated and the relative displacement is initiated by a control unit 16. Synchronously with the relative displacement, the computer 9 calculates the shadowgraph deriving from the obtained data and effects reproduction thereof on the monitor 10 in real time. When the physician recognizes the desired measurement field in the shadowgraph, then he or she releases the key 15 and the exposure of the shadowgraph is ended.

It will be understood by those skilled in the art that some functional blocks shown in the computer 9 for use in calculating the shadowgraph may be shaved for use in calculating the tomogram. Since the tomogram is calculated in a known manner, however, this has been schematically indicated by the stage 18 for clarity, but two completely separate data processing paths, one for the shadowgraph and one for the tomogram, need not necessarily be present.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical imaging apparatus comprising:
   measurement means for conducting a scan of an examination subject, said measurement means including an x-ray source and a radiation detector rotatable around said examination subject for irradiating said examination subject with an x-ray beam from said x-ray source at at least one projection angle, said radiation detector generating electrical output signals corresponding to radiation incident thereon at each projection angle;
   means for effecting relative longitudinal displacement between said measurement means and said examination subject;
   means for calculating a shadowgraph of said examination subject in real time as said relative longitudinal displacement takes place, from output signals with said measurement means disposed at a selected projection angle a plurality of times during said scan; and
   means for displaying said shadowgraph, as said shadowgraph is calculated, to an extent correlated with the amount of relative longitudinal displacement between said examination subject and said measurement means.

2. A medical imaging apparatus as claimed in claim 1 wherein said measurement means includes an x-ray source and a radiation detector rotatable around said examination subject for irradiating said examination subject with an x-ray beam from said x-ray source at a plurality of projection angles, and further comprising means for calculating and displaying a tomographic image of said examination subject from said output signals.

3. A medical imaging apparatus comprising:
   measurement means for conducting a scan of an examination subject, including an x-ray source and a radiation detector rotatable around an examination subject for irradiating said examination subject with an x-ray beam from said x-ray source at at least one projection angle, said radiation detector extending in a direction designated $\beta$ and generating electrical output signals corresponding to radiation incident thereon at each projection angle;
   means for effecting relative displacement in a longitudinal direction between said measurement means and said examination subject;
   means for calculating a shadowgraph of said examination subject in real time as said relative displacement takes place by convolution of said output signals, with said measurement means disposed at a selected projection angle a plurality of times during said scan, according to the equation:

$$b_l(k) = \sum_{\chi=-n/2}^{n/2} U_l(k - \chi) \times h(\chi),$$

wherein
l denotes the index in the $\beta$-direction, k denotes the index in the longitudinal direction, $\chi$ denotes the numerical index for the convolution, $u_l(k)$ denotes the output signals convolved in the $\beta$-direction, $b_l(k)$ denotes the output signals additionally convolved in the longitudinal direction, h denotes the convolution core and n denotes the degree of the convolution core; and
   means for displaying said shadowgraph, as said shadowgraph is calculated, to an extent correlated with the amount of relative displacement between said examination subject and said measurement means.

4. A medical imaging apparatus as claimed in claim 3 wherein said measurement means includes an x-ray source and a radiation detector rotatable around said examination subject for irradiating said examination subject with an x-ray beam from said x-ray source at a plurality of projection angles, and further comprising means for calculating and displaying a tomographic image of said examination subject from said output signals.

* * * * *